US007077837B2

(12) United States Patent
Sahagian

(10) Patent No.: US 7,077,837 B2
(45) Date of Patent: Jul. 18, 2006

(54) MULTI-LAYERED RADIOPAQUE COATING ON INTRAVASCULAR DEVICES

(75) Inventor: Richard Sahagian, Burlington, MA (US)

(73) Assignee: Implant Sciences Corporation, Wakefield, MA (US)

(*) Notice: Subject to any disclaimer, the term of this patent is extended or adjusted under 35 U.S.C. 154(b) by 0 days.

(21) Appl. No.: 09/999,349

(22) Filed: Nov. 15, 2001

(65) Prior Publication Data

US 2002/0138130 A1    Sep. 26, 2002

Related U.S. Application Data

(60) Provisional application No. 60/252,005, filed on Nov. 20, 2000, provisional application No. 60/253,107, filed on Nov. 27, 2000.

(51) Int. Cl.
*A61F 2/06* (2006.01)
(52) U.S. Cl. ...................... 606/1.15; 427/531
(58) Field of Classification Search .............. 623/1.15, 623/1.12, 1.13, 1.34, 1.46, 1.44, 1.45; 427/2.25, 427/2.24, 446, 456, 528, 531, 564
See application file for complete search history.

(56) References Cited

U.S. PATENT DOCUMENTS 4,672,970 A * 6/1987 Uchida et al. .............. 600/360
5,679,470 A   10/1997 Mayer ........................ 428/662
5,858,556 A    1/1999 Eckert et al. ............... 428/586
5,919,126 A *  7/1999 Armini .......................... 600/3
6,099,561 A    8/2000 Alt ............................ 623/1.44
6,174,329 B1 * 1/2001 Callol et al. ............... 623/1.34
6,315,794 B1 * 11/2001 Richter ...................... 623/1.34
6,387,123 B1   5/2002 Jacobs et al. ............. 623/1.34
6,451,373 B1 * 9/2002 Hossainy et al. .......... 427/2.25

FOREIGN PATENT DOCUMENTS

EP        0 916 317 A1    5/1999
WO        WO 00/54704     9/2000

OTHER PUBLICATIONS

Richard Sahagian; Critical Insight: Marking Devices with Radiopaque Coatings; Medical Device & Diagnostic Industry, May 1999; Copyright © 1999 Canon Communications LLC.

* cited by examiner

*Primary Examiner*—(Jackie) Tan-Uyen T. Ho
(74) *Attorney, Agent, or Firm*—Muirhead and Saturnelli, LLC

(57) ABSTRACT

Intravascular devices having a radiopaque layer thereon for visualization are provided. The devices further includes a capping layer on the radiopaque layer to prevent exposure of the radiopaque material to surrounding tissues. A method of coating the device is also provided. The method includes using an unbalanced magnetic field magnetron to generate, from a source, metal atoms for coating and bombarding ions for compressing deposited metal atoms to the surface of the device.

24 Claims, 8 Drawing Sheets

Multilayered Microfused Radiopaque Coating
With Adhesion Interlayer

Figure 1. A stent deployed in the length of an artery having an occlusion. The proper placement of stent is critical to the successful outcome of the procedure.

Multilayered Microfused Radiopaque Coating With Adhesion Interlayer

MULTI-LAYERED RADIOPAQUE COATING ON INTRAVASCULAR DEVICES

RELATED U.S. APPLICATION(S)

This application claims priority to U.S. Provisional Application Ser. Nos. 60/252,005, filed Nov. 20, 2000, and 60/253,107, filed Nov. 27, 2000, both of which are hereby incorporated herein by reference.

FIELD OF THE INVENTION

The present invention relates to intravascular devices, and in particular, to intravascular devices having radiopaque coatings thereon for visualization.

BACKGROUND ART

Many medical intravascular devices are used either temporarily or permanently inside the human body. An example of such an intravascular device includes a stent for use in, for instance, coronary angioplasty. Stents are small metal scaffolds used to mechanically hold open and support constricted coronary arteries. For proper positioning, stents may need to be visualized during and after deployment using imaging techniques such as x-ray radiography and x-ray fluoroscopy. However, due to the nature of the materials used to construct these intravascular devices and their small size, visualization of these devices can often be poor or non-existent.

Certain "radiopaque" materials are known to be more effective in stopping energetic x-ray photons, and as a result, are more readily visualized during, for instance, x-ray imaging. However, incorporation of these radiopaque materials, including ones that are biocompatible, into the device substrate material can have an undesirable effect on other device characteristics, such as mechanical performance.

Traditional methods for adding opacity to a device include the use of metal bands, electrochemical deposition (i.e., electroplating), or coatings. In the case of metal bands or disks having radiopaque material, the bands or disks may be crimped, swaged, pressed or glued on to the device at selected points. However, bands have the potential for becoming loose, shifting, or even falling off. Moreover, bands may also cause abrasion to the intima (i.e., the lining of a vessel wall) during insertion of the device, especially if the bands have sharp edges or outward projections. The physiological response can often be a reclosure of the lumen, thereby negating the effect of the device. Additionally, cellular debris can be trapped between the intravascular device and the band, and the edges of the band can serve as a site for thrombus formation.

Alternatively, a metal coating can be used as a marker and can be applied on to an intravasuclar device using chemical vapor deposition (CVD), physical vapor deposition (PVD), or electroplating. However, for the range of thickness required to make the coating x-ray opaque, CVD and conventional PVD methods do not appear to provide a coating which can exhibit sufficient adhesion to the surface of the device, especially a stainless steel substrate surface, to be reliable in a medical device application.

On the other hand, electroless and/or electroplated coatings are often porous, and can present a biocompatibility problem, since the porous coating can act to entrap the plating chemicals. For devices constructed from, for instance, titanium alloys, embrittlement caused by the electroplating process can occur to significantly alter the mechanical properties and thus the function of the device.

Ion beam assisted deposition (IBAD) of radiopaque materials has been used and can improve the adhesion of coatings to the substrate surface. IBAD employs conventional PVD to create a vapor of atoms of, for instance, a noble metal that coats the surface of the substrate, while simultaneously bombarding the substrate surface with ions at energies, typically in the range of 0.8 to 1.5 keV, to impact and condense the metal atoms on the substrate surface. An independent ion source is used as the source of ions.

Coatings produced by traditional IBAD, however, are costly. When evaporating, atoms of expensive noble metal are emitted over a large solid angle compared to that subtended by the device or devices being coated, thus requiring a costly reclaiming process. Moreover, because an evaporator uses a molten metal, it must be located upright on the floor of the deposition chamber to avoid spilling, thereby restricting the size and configuration of the chamber and the devices being coated. Additionally, evaporators cannot deposit mixtures of alloys effectively because of the differences in the alloy components' evaporation rates. As such, the composition of the resulting coating constantly changes.

Furthermore, with IBAD, the flux (i.e. stream) of bombarding ions and evaporant (i.e., atoms of metal being deposited) approach the substrate from different directions. To this end, the energy from the bombarding ions transferred to the evaporant atoms varies depending on the extent to which the two streams overlap. As a result, the growth mechanism of the coating can be inconsistent, and uniform coating properties are difficult to achieve even over the same device.

SUMMARY OF THE INVENTION

The present invention provides, in accordance with one embodiment, an intravascular device having substrate, a layer of a radiopaque material disposed on the substrate surface and having a thickness sufficient for visualization, and a capping layer to prevent exposure of the layer of radiopaque material to surrounding tissue. In an embodiment, the device may include a transition layer between the layer of radiopaque material and the capping layer to enhance bonding of the capping layer to the layer of radiopaque material. The device may also include an adhesion layer to promote bonding of the layer of radiopaque material to the substrate.

The present invention also provides, in another embodiment, a method for coating an intravascular device for visualization. The method includes providing an intravascular device having a substrate surface. Next, a flux of atoms of a radiopaque material and a flux of bombarding ions may be generated in a manner which permits the flux of atoms of a radiopaque material and bombarding ions to travel towards the substrate surface of the device in a co-linear fashion. Thereafter, the atoms of radiopaque material may be deposited onto the substrate surface, and the bombarding ions permitted to impact the atoms of the radiopaque material deposited on the substrate surface to provide a substantially uniform layer of radiopaque material. If desired, co-linear fluxes of metal atoms and of bombarding ions and may be directed in a similar manner on to the layer of radiopaque material to provide a capping layer.

DESCRIPTION OF VARIOUS EMBODIMENTS

Figure 1:
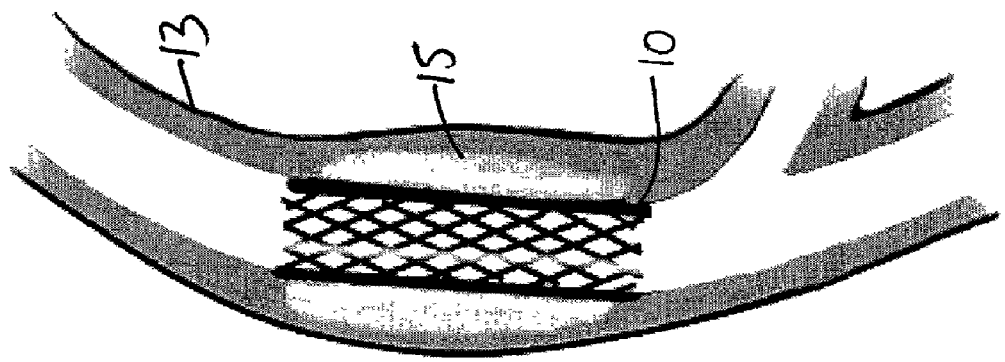
FIG. 1 illustrates an instravascular device in accordance with one embodiment of the present invention.

In FIG. 1, there is shown an intravascular device 10 in accordance with one embodiment of the present invention. The device 10, as illustrated by the cross sectional view in FIG. 2, includes a body 11 having substrate surface 12, a layer 14 of a radiopaque material on the substrate surface 12, and a capping layer 16 on the layer 14 of the radiopaque material.

The device 10, illustrated in FIG. 1 as a stent, may be made so that the body 11 can be provided with the ability to expand while, at the same time, being flexible, so that the device 10 can be deployed to a site of stenosis 15 within, for instance, a coronary artery 13. In addition, the body 11 of device 10 may be made from a strong material sufficient to provide adequate radial strength at the site of stenosis to prevent closure. In one embodiment, the body 11 of device 10 may be made from a metallic material, which includes, but is not limited to, stainless steel, nickel-based steel, cobalt-chrome, titanium alloys, and nitinol.

Figure 2:
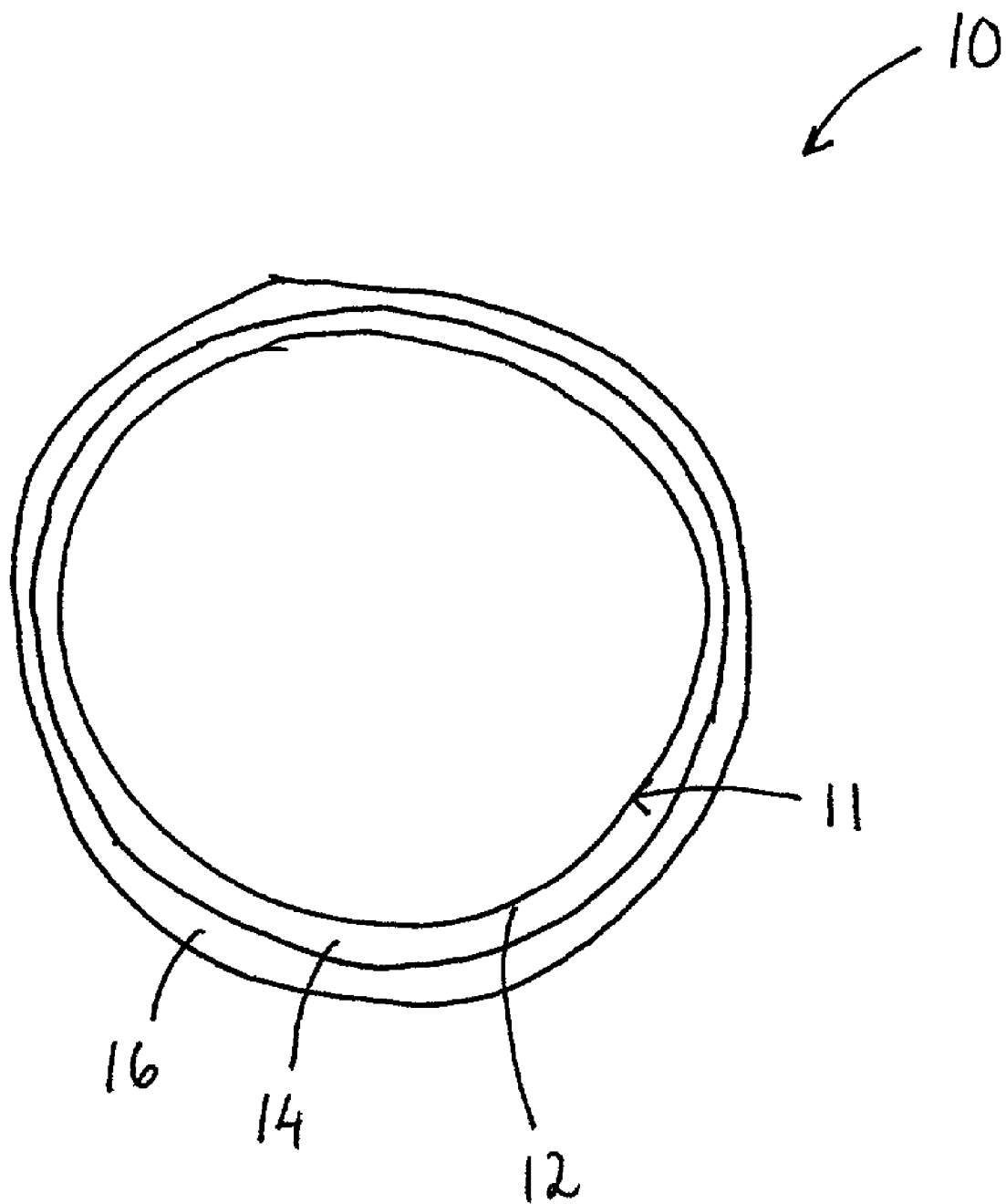
FIG. 2 illustrates a cross sectional view of the intravascular device shown in FIG. 1.
Figure 3:
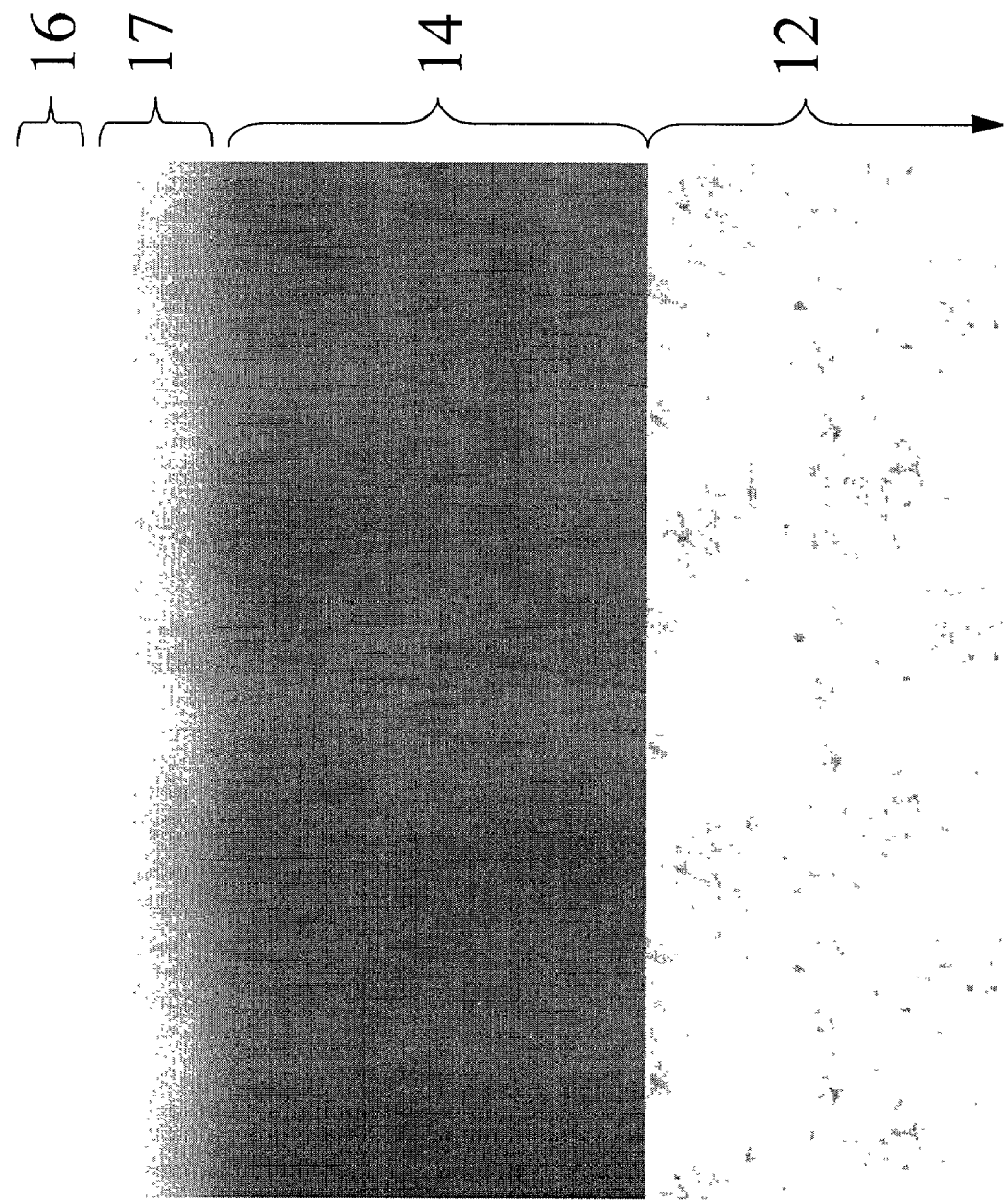
FIG. 3 illustrates a detailed cross sectional view of an intravascular device in accordance with one embodiment of the present invention.

With reference now to FIGS. 2 and 3, the layer 14 of radiopaque material provides the device 10 with opacity, so that the device 10 may be visualized by, for instance, x-ray imaging. In addition to providing opacity, the layer 14 may be pliable and malleable to permit the layer 14 to expand and flex along with the body 11 of device 10. To that end, the layer 14 may be made from a ductile metal, for instance a noble metal, an example of which may be gold. The layer 14 should also be substantially pure and free of contaminating material, so as to minimize interference with its bond to the substrate surface 12. Furthermore, to permit sufficient opacity, while maintaining flexibility and malleability, the layer 14, in accordance with an embodiment of the invention, may be provided with a thickness having a range of from about 1 micron to about 15 micron, with a preferred thickness having a range of from about 3 microns to about 9 microns. In the instance where gold may be used for layer 14, a thickness ranging from about 5 microns to about 6 microns is preferred. The thickness of the layer 14 of radiopaque material may vary depending on the type of application or use for which the device 10 is employed.

In certain situation, it may not be desirable to expose the layer 14 of radiopaque material to surrounding tissues. To that end, capping layer 16 may be provided to prevent exposure of surrounding tissues to the radiopaque material on device 10. It should be noted that the integrity of the capping layer 16 must be maintained while the device 10 is being maneuvered and deployed. Accordingly, the capping layer 16 may be made from a strong, substantially scratch resistant, yet malleable material with a thickness ranging from about 0.5 micron to about 1 micron. In addition, as the capping layer 16 may be positioned adjacent living tissues, it may be desirable to manufacture the capping layer 16 from a biocompatible material. In an embodiment of the invention, the capping layer 16 may be made from a metallic material, including platinum alloys, platinum-iridium, palladium, and tantalum. The capping layer 10, like the layer 14 should be substantially pure and free of contaminating material.

With particular reference now to FIG. 3, to enhance a bond between the capping layer 16 and the layer 14 of radiopaque material, the device 10 may be provided with a transition layer 17. The transition layer 17, in one embodiment, comprises a mixture of the radiopaque material and the material comprising the capping layer 16, for example, a mixture of gold or platinum-iridium. Such a mixture can provide a graded interface between the capping layer 16 and the layer 14 of radiopaque material which, it has been found, can result in superior adhesion between the two layers 14 and 16. It is noted that providing the transition layer 17 with a thickness of about 1 micron or less, and in particular, a thickness ranging from about 0.25 micron to about 0.5 micron, can add to the superior adhesion between the capping layer 16 and the layer 14 of radiopaque material, while maintaining the diameter of the device 10 within an optimal range.

Figure 4:
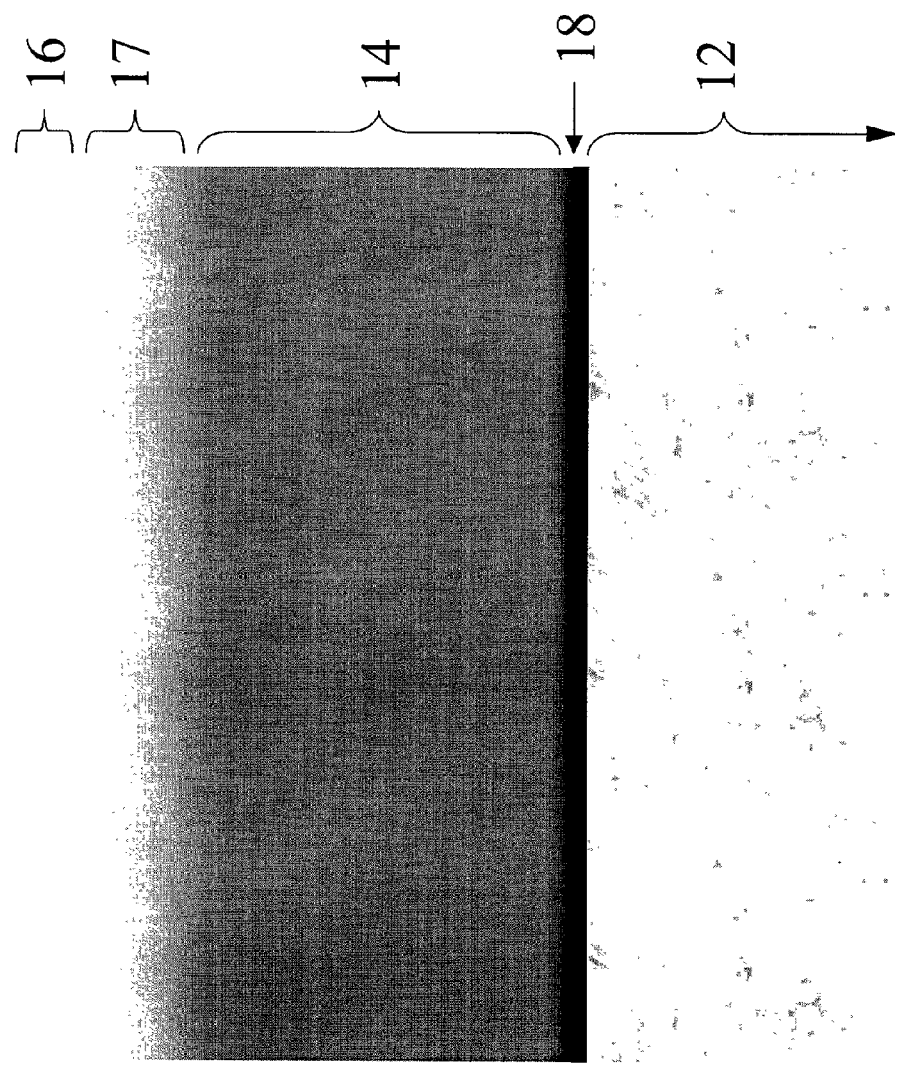
FIG. 4 illustrates a detailed cross sectional view of an intravascular device in accordance with another embodiment of the present invention.

Now referring to FIG. 4, in certain embodiments, an adhesion layer 18 may be provided between the substrate surface 12 and the layer 14 of radiopaque material to enhance the bonding of the layer 14 to the substrate surface 12. The adhesion layer 18, in an embodiment, includes a mixture of chromium, palladium, and the radiopaque material. Such a mixture, similar to the mixture in the transition layer 17, provides a graded interface to which the layer 14 of radiopaque material can better adhere. In order to maintain the diameter of device 10 within an optimal range, the adhesion layer 18 may be provided with a thickness that is about 1 micron or less, and more particularly, from about 0.25 microns to about 0.5 microns.

Figure 5:
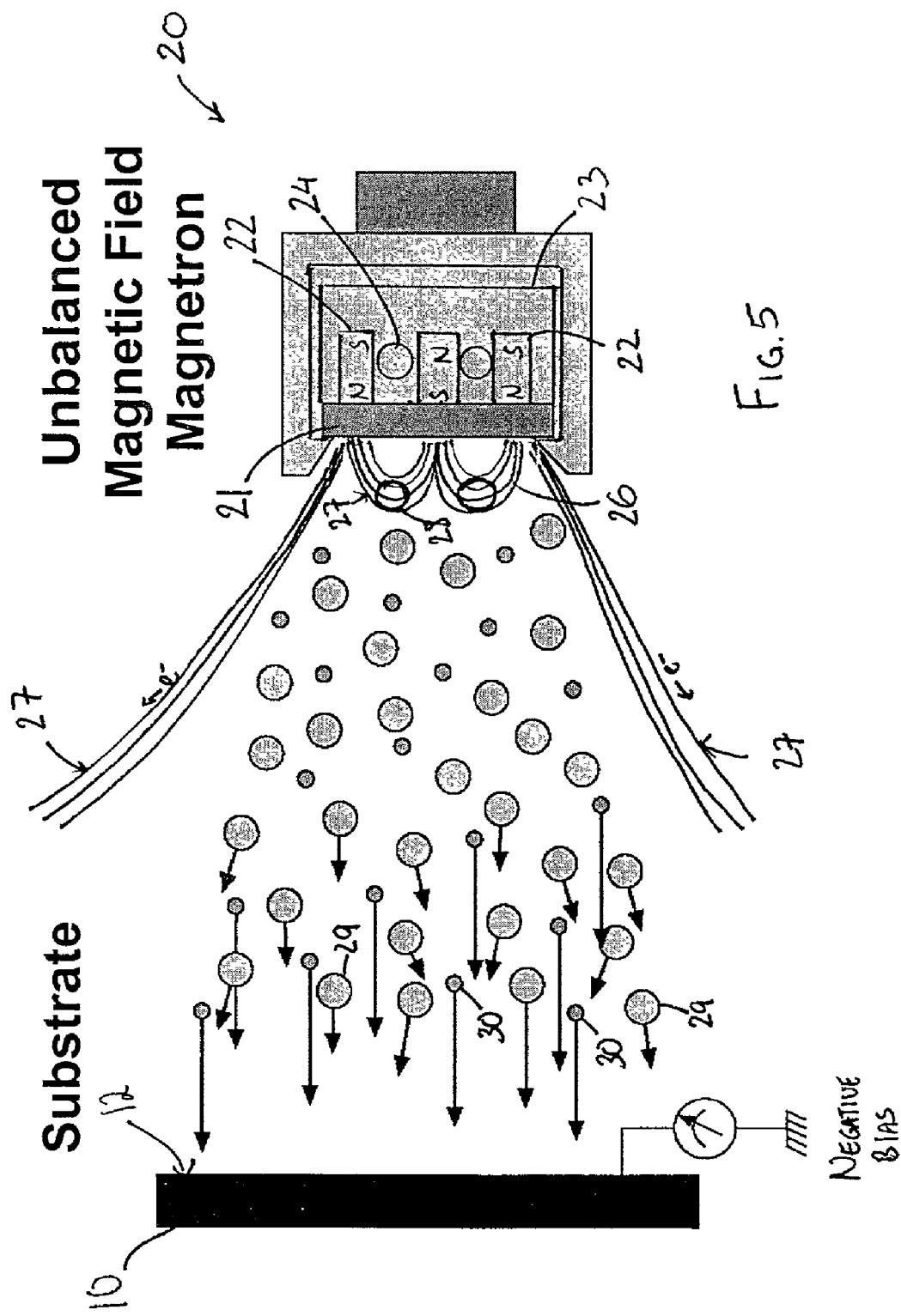
FIG. 5 illustrates a method for depositing various layers onto an intravascular device in accordance with an embodiment of the present invention.

Referring now to FIG. 5, the various layers described above may be deposited on the device 10 using, in one embodiment, an unbalanced magnetic field magnetron 20. The magnetron 20, as shown in cross sectional view in FIG. 5, includes a source 21 of metal atoms for use in coating the device 10. The source 21, typically a plate comprising the metal atoms for coating, may be positioned in front of an array of magnets 22 placed within a cooling block 23. The cooling block 23, in an embodiment, may be made from, for instance, copper. If desired, cooling channels 24 may be provided within the cooling block 23 to permit fluid, like water, to circulate therethrough to cool down the magnetron 20.

Figure 6:
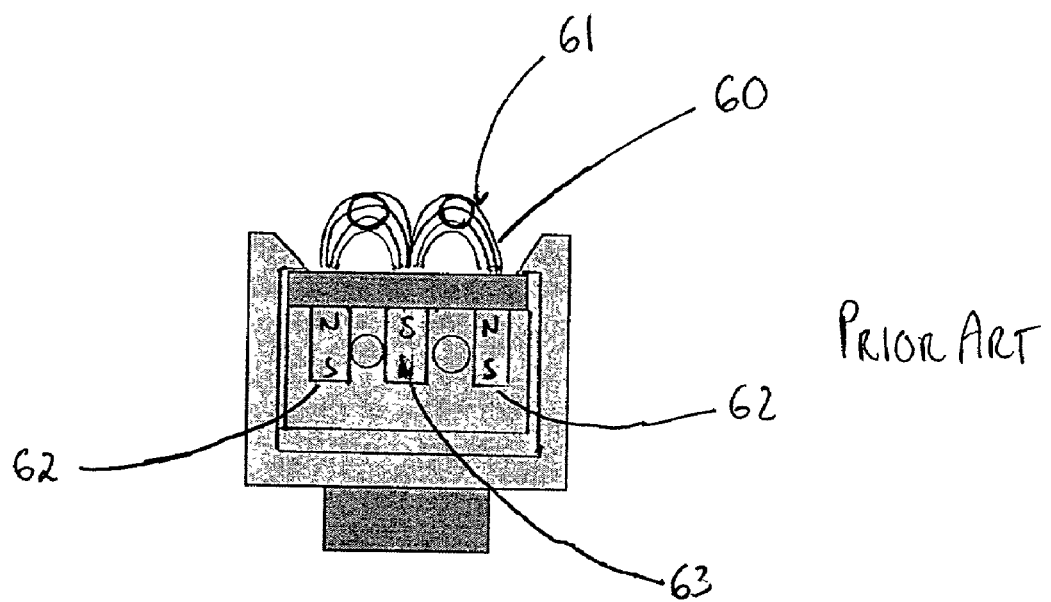
FIG. 6 illustrates a standard prior art magnetron.

The array of magnets 22 within the cooling block 23 preferably permits the magnetron 20 to generate an unbalanced magnetic field 26 when the cooling block 23 is biased with an electrical charge ranging from about −200 VDC to about −100 VDC. It should be noted that in a standard (i.e., balanced magnetic field) magnetron, as shown in FIG. 6, the field lines 61 in the magnetic field 60 emanate from the outer magnets 62 and terminate tightly in the central magnet 63.

However, by providing the magnetron 20 (FIG. 5) of the present invention with magnets 22 of uneven strength, for example, outer magnets that are stronger than central magnet, not all field lines 27 emanating from the outer magnets terminate in the central magnet. These field lines 27, of course, eventually returns to the array of magnets, but not in a tight pathway as that observed with field lines in the standard magnetron. It should be noted that although the array of magnets 22 in FIG. 5 is arranged in a circular format, the array can be arranged in any geometric shape, so long as an appropriate unbalanced magnetic field can be generated.

Figure 7:
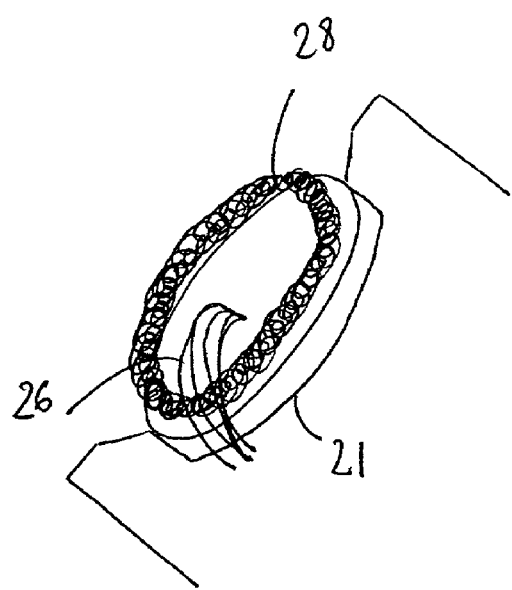
FIG. 7 illustrates a plasma cloud generated on a magnetron of the present invention.

The magnetic field 26, which has electrons trapped therein, in the presence of noble atoms, for instance, argon or xenon atoms, can cause an ionization event to create a plasma cloud 28 within the magnetic field 26. In particular, when noble atoms traveling through the magnetic field 26 come into contact with the electrons therein, the noble atoms become ionized (i.e., positively charged ions). This ionization process generates a plasma cloud 28 within the magnetic field 26. As illustrated in FIG. 7, the plasma cloud 28 above the source plate 21 and within the magnetic field 26 can conform to the shape of the array of magnets 22. In this instance, the plasma cloud 28 is toroidal in shape.

It should be noted that since the cooling block 23 is biased with a negative electrical charge, the positively charged noble ions within the plasma cloud 28 are drawn towards the source 21 of metal atoms positioned in front of the array of magnets 22. In addition, since the magnetic field 26 is unbalanced, the plasma cloud 28 may not be as well contained therein, making it easier to extract or draw the noble ions from the plasma cloud 28 towards source 21. Upon hitting the source 21 of metal atoms, the noble ions can cause metal atoms 29 to come off the surface of the source 21 (i.e., sputtering) and travel towards the device 10. Because of the manner in which the noble ions impinge the surface of the source 21, the metal atoms 29 coming of the source tend to travel in a substantially straight path towards the substrate surface 12 of device 10. The movement of metal atoms towards the device 10 creates what is know as a flux of metal atoms 29. The flux of metal atoms 29, upon hitting the substrate surface 12 of device 10, coats the substrate surface 12 with a layer of the metal atoms 29.

The presence of an unbalance magnetic field 26 on the magnetron 20 also makes it less difficult for some of electrons within the plasma cloud 28 to escape therefrom. These escaping electrons tend to follow field lines 27 away from plasma cloud 28, leaving the plasma cloud 28 net positive. Since the cloud 28 generally would want to remain net neutral, noble ions 30 are permitted to escape towards the substrate surface 12 of the device 10. This flux of noble ions 30, upon bombarding the substrate surface 12, act to impact and condense the metal atoms 29 onto the substrate surface 12. In this manner, a layer of metal atoms 29 having uniform thickness throughout may be generated. It should be appreciated that the escaping electrons may collide with noble atoms present in an area between the magnetron 20 and the device 10. When such an event occurs, additional noble ions 30 can be generated to bombard the substrate surface 12 to impact and condense the metal atoms 29 on the substrate surface 12.

To further enhance the movement of positively charged noble ions 30 towards the device 10, the device 10 may be biased with an electrical charge ranging from about −20 VDC to about −100 VDC. The biasing of the device 10 with a negative voltage can further generate a desired effect. In particular, a negative charged device 10 can reduce the number of electrons that may impinge on the device 10. In this manner, the amount of heat typically generated from electrons hitting the device 10 can be minimized.

It should be noted that unlike existing technology which employs different independent sources for generating coating metal atoms and for generating bombarding noble ions (e.g., IBAD), the unbalanced magnetic field magnetron 20 of the present invention permits bombarding noble ions 30 to be generated from the same source, that is the plasma cloud 28, used to generate metal atoms 29 for coating the device 10. In addition, while the magnetron 20 of the present invention permits the flux of metal atoms 29 and flux of bombarding ions 30 to both travel in a co-linear, or same, direction from the plasma cloud 28 towards the device 10, it can also control the ratio of bombarding ions flux to metal atoms flux, so that such ratio can be maintained at a substantial constant. The ability to impart a co-linear flow and the ability to maintain a constant ratio of metal atoms to bombarding noble ions further enhances the generation of a substantially uniform coating on the device 10. Furthermore, energy imparted by the bombarding ions, typically in the range of from about 50 eV to about 250 eV, is substantially less than that observed with the IBAD method (e.g., 0.8 keV to 1.5 keV). By imparting relatively less energy per bombarding ion but to relatively more bombarding ions, the unbalanced magnetic field magnetron 20 can increase compression events of the metal atoms deposited on the substrate surface 12, while decreasing the likelihood of back-sputtering of metal atoms from the substrate surface 12.

Figure 8A:
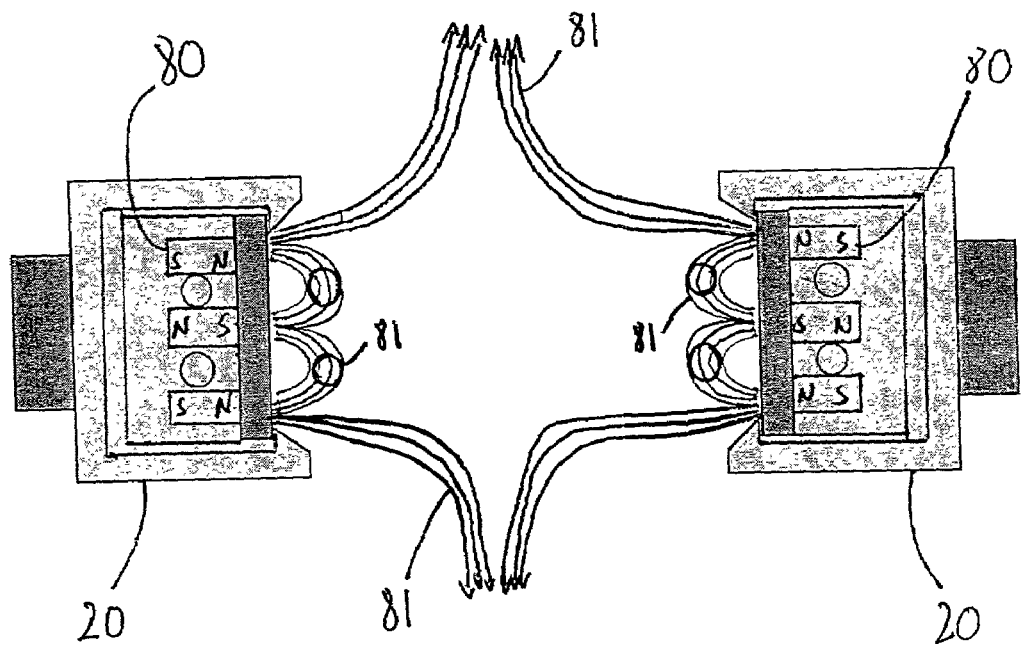
FIGS. 8A–B illustrate various configurations of magnetrons for use in accordance with embodiments of the present invention.
Figure 8B:
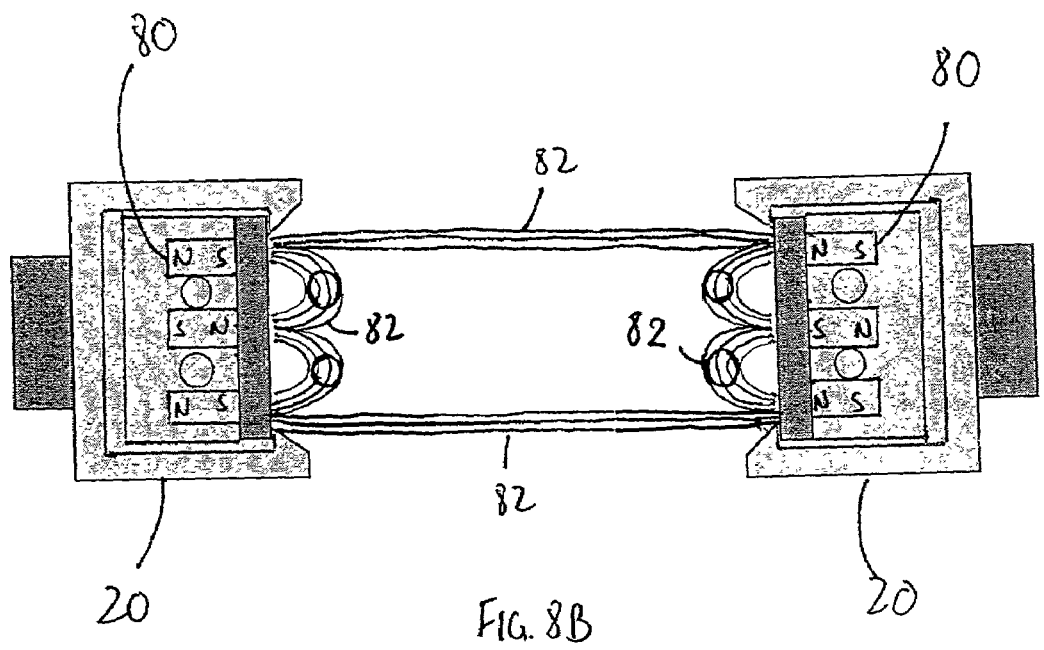

Although the description above references one magnetron 20 in the coating of device 10, it should be appreciated that multiple magnetrons 20, such as that shown in FIGS. 8A–B may be used, especially if multiple metal atoms are used to provide multiple layers on the device 10. In an embodiment wherein at least two magnetrons 20 are used, the magnetrons may be set up in mirrored fashion or in coupled fashion.

In the mirrored fashion, as illustrated in FIG. 8A, each magnet 80 in one magnetron 20 may be situated so that it faces a magnet 80 in the opposing magnetron 20 having a same magnetic pole. By positioning the magnets 80 in this mirrored fashion, magnetic fields 81, such as that shown in FIG. 8A, can be generated to permit relatively few ionizing events, so as to reduce the amount of noble ion bombardment of the substrate surface.

In the coupled fashion, as illustrated in FIG. 8B, each magnet 80 in one magnetron 20 may be situated so that it faces a magnet 80 in the opposing magnetron 20 having an opposite magnetic pole. By positioning the magnets 80 in the coupled fashion, magnetic fields 82, such as that shown in FIG. 8B, can be generated to permit relatively more ionizing events, so as to increase the amount of noble ion bombardment of the substrate surface.

An example for coating the device 10 is hereinafter provided. In one embodiment of the invention, device 10, which in this example may be a stent approximately 2.5 cm in length and approximately 4 mm in diameter, may first be cleaned using any number of appropriate solvent cleaning protocols designed to remove contaminants on all surfaces of the device 10. The device 10 may subsequently be dried.

Next, an ion pre-clean process may be employed to further clean the surface 12 of device 10 prior to coating.

Figure 9:
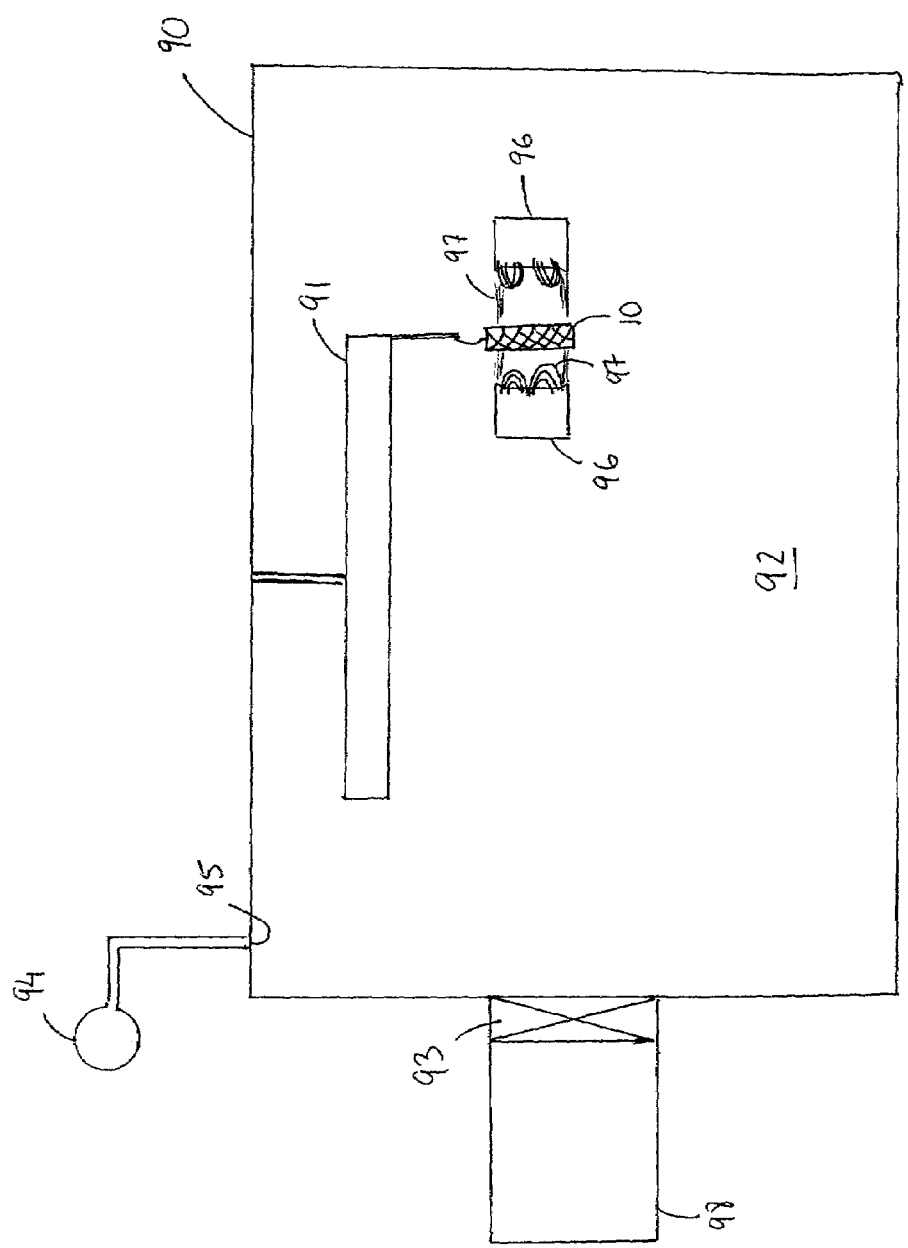
FIG. 9 illustrates a coating apparatus for use in the manufacturing of a device of the present invention.

Looking now at FIG. 9, the device 10 may be taken to a coating apparatus 90 and placed on a fixture 91 positioned within a vacuum chamber 92. Next, a vacuum of about 1E-3 to 1E-9 torr may be drawn from chamber 92 using vacuum pump 98. Vacuum pumping may thereafter be throttled by valve 93 and a noble gas, for instance, argon or xenon, may be introduced from a source 94 through port 95 into chamber 92. The chamber 92 may continue to be filled with the noble gas to a pressure ranging from about 0.1 mtorr to about 100 mtorr. Next, an electrical charge of about −200 VDC to about −1000 VDC may be applied to device 10, while the device 10 is moved through a magnetic field between the magnetrons 96. In the presence of the electrical charge, the noble atoms become ionized and are pulled toward the surface of the device 10 to rid the surface of oxides and other unwanted contaminants. This pre-cleaning process of the device 10 may last from about 5 to about 60 minutes, depending on the initial cleanliness of the device 10.

Once the ion pre-cleaning process is completed, the coating process may begin. Vacuum pumping in chamber 92 may be throttled further and a noble gas, such as argon, may be introduced through port 95 at a rate of about 33 sccm (standard cubic centimeter) and to a pressure of from about 1 mtorr to about 20 mtorr within the chamber 92. The magnetrons 96 may next be electrically charged to a voltage in the range of from about −500 VDC to about −1000 VDC. In the presence of the electrical charge, the noble gas becomes ionized to generate a plasma cloud within the magnetic field 97 on each of the magnetrons 96. In one embodiment, the magnetrons 96 may be placed approximately 8 in. apart with the device 10 positioned in therebetween. If desired, one magnetron 96 may be oriented at an angle of plus 20°, while the other magnetron 96 may be oriented at an angle of minus 20° from the normal of an outer surface device 10 to enhance deposition on to surfaces of the three-dimensional device 10. Subsequently, a charge of about −40 VDC may be applied to the device 10, so that a current draw on the device 10 cab be maintained at about between 7 to 9 mA. Thereafter, metal atoms, such as gold, on one magnetron 96, may be deposited on to the device 10 at a rate, for example, of between 165–185 Å/min. The rate of deposition should be such that the ratio between the metal atoms flux and the bombarding ions flux can be maintained at a substantial constant. The constant, as it will be appreciated, can vary depending on the device being coated. After between about 7.5 and about 8.0 microns have been deposited, the gold deposition may be stopped to provide a radiopaque layer. Next, metal atoms, such as platinum or platinum-irridium, on the opposing magnetron 96, may be deposited at a similar rate to a thickness of between about 0.5 and about 1.0 micron to provide a capping layer. After an appropriate cooling period, the vacuum chamber 92 may be vented to atmosphere using nitrogen gas, and the device 10 removed.

It should be appreciated that a transition layer 17, such as that shown in FIG. 3, may be provided between the capping layer 16 and the radiopaque layer 14 to enhance bonding between the two layers 14 and 16. To deposit the transition layer 17 onto the device 10, the magnetron depositing, for instance, gold atoms onto the device 10, may be controlled to decrease the amount at which gold atoms are being deposited, while the opposing magnetron used for depositing platinum atoms or a mixture of platinum-iridium atoms may be controlled to simultaneously deposit the platinum or platinum-iridium atoms at an increasing amount. The amount of platinum or mixture of platinum-iridium atoms being deposited can continue to increase, while the amount of gold atoms being deposited can continue to decrease until platinum or mixture of platinum-iridium atoms comprise 100 percent of the deposition. Such a process can provide a graded transition layer 17, preferably with a thickness ranging from about 0.25 microns to about 0.5 microns, which can result in superior adhesion of the capping layer 16 to the radiopaque layer 14.

An adhesion layer 18, such as that shown in FIG. 4, may also be deposited between the substrate surface 12 and the layer 14 of radiopaque material. To deposit the adhesion layer 18 onto the substrate surface 12, one magnetron may be used to generate a flux of chromium atoms onto the substrate surface 12. Thereafter another magnetron may be used to generate a flux of palladium atoms, so that the palladium atoms may be simultaneously deposited onto the substrate surface 12 with the chromium atoms. The magnetron generating the chromium flux may next be controlled to decrease the amount at which chromium atoms are being deposited, while the opposing magnetron used for generating the palladium flux may be controlled to increase the amount at which palladium atoms are being deposited. This process can continue until palladium atoms comprise 100 percent of the deposition. At a point at which only palladium atoms are being deposited, a flux of gold atoms may be generated for deposition onto the substrate surface 12. The amount of palladium atoms being deposited thereafter may be decreased, while the amount of gold atoms being deposited may be increased, until gold atoms comprise 100 percent of the deposition. Such a process can provide a graded adhesion layer 18, preferably with a thickness ranging from about 0.1 micron to about 0.2 microns, which can result in superior adhesion of the layer 14 of radiopaque material to the substrate surface.

Alternatively, instead of generating a flux of chromium atoms and a flux of palladium atoms from different magnetrons, a mixture of chromium-palladium atoms may be positioned on one magnetron to permit a flux of chromium-palladium atoms to be generated. The amount of chromium-palladium atoms being deposited may thereafter be decreased, while the amount of gold atoms being deposited may be increased, until gold atoms comprise 100 percent of the deposition.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. An intravascular device comprising:
    a substrate surface;
    a layer of a radiopaque material on the substrate surface and having a thickness sufficient to permit visualization;
    a capping layer positioned on the layer of radiopaque material to prevent exposure of the layer of radiopaque material to surrounding tissue; and
    at least one adhesion layer disposed between the radiopaque material and the substrate surface, wherein a first part of the adhesion layer adjacent to the substrate surface has a different composition than a combination of the radiopaque material and a material in the substrate surface and wherein a second part of the adhesion layer adjacent to the layer of radiopaque material has a combination of the material used for the first part of the adhesion layer and the radiopaque material.

2. An intravascular device as set forth in claim 1, wherein the substrate surface comprises a metallic material.

3. An intravascular device as set forth in claim 2, wherein the metallic material includes one of stainless steel, nickel-based steel, cobalt-chrome, titanium alloys, and nitinol.

4. An intravascular device as set forth in claim 2, wherein the metallic material is flexible.

5. An intravascular device as set forth in claim 1, wherein the layer of radiopaque material is made from a pliable and malleable material to provide the layer with flexibility.

6. An intravascular device as set forth in claim 1, wherein the layer of radiopaque material comprises gold.

7. An intravascular device as set forth in claim 1, wherein the layer of radiopaque material has a thickness ranging from about 1 micron to about 15 microns.

8. An intravascular device as set forth in claim 1, wherein the capping layer comprises a biocompatible material.

9. An intravascular device as set forth in claim 8, wherein the biocompatible material comprises a metallic material.

10. An intravascular device as set forth in claim 9, wherein the metallic material includes one of platinum alloys, platinum-iridium, palladium, and tantalum.

11. An intravascular device as set forth in claim 1, wherein the capping layer has a thickness ranging from about 0.5 micron to about 1.0 micron.

12. An intravascular device as set forth in claim 1, further including a transition layer situated between the capping layer and the layer of radiopaque material to enhance bonding between the capping layer and the layer of radiopaque material.

13. An intravascular device as set forth in claim 12, wherein the transition layer comprises a mixture of the radiopaque material and material comprising the capping layer.

14. An intravascular device as set forth in claim 13, wherein the transition layer comprises a mixture of gold and platinum-iridium.

15. An intravascular device as set forth in claim 13, wherein the transition layer has a thickness ranging from about 0.25 microns to about 0.5 microns.

16. An intravascular stent comprising:
a flexible expandable body having a surface;
a layer of a radiopaque material on the surface and having a thickness sufficient to permit visualization;
an adhesion layer between the layer of radiopaque material and the surface to enhance bonding between the layer of radiopaque material and the surface; and
a capping layer positioned on the layer of radiopaque material to prevent exposure of the layer of radiopaque material to surrounding tissue, wherein a first part of the adhesion layer adjacent to the flexible expandable body has a different composition than a combination of the radiopaque material and a material in the flexible expandable body and wherein a second part of the adhesion layer adjacent to the layer of radiopaque material has a combination of the material used for the first part of the adhesion layer and the radiopaque material.

17. An intravascular stent as set forth in claim 16, wherein the layer of radiopaque material is made from a pliable and malleable material to provide the layer with flexibility.

18. An intravascular stent as set forth in claim 16, wherein the capping layer comprises a biocompatible material.

19. An intravascular stent as set forth in claim 16, wherein the layer of radiopaque material comprises gold.

20. An intravascular stent as set forth in claim 16, wherein the capping layer includes one of platinum alloys, platinum-iridium, palladium, and tantalum.

21. An intravascular stent as set forth in claim 16, further including a transition layer situated between the capping layer and the layer of radiopaque material to enhance bonding between the capping layer and the layer of radiopaque material.

22. An intravascular device as set forth in claim 21, wherein the transition layer has a thickness ranging from about 0.25 microns to about 0.5 microns.

23. An intravascular stent as set forth in claim 21, wherein the transition layer comprises a mixture of the radiopaque material and material comprising the capping layer.

24. An intravascular stent as set forth in claim 21, wherein the transition layer comprises a mixture of gold and platinum-iridium.

* * * * *